(12) United States Patent
Galloway et al.

(10) Patent No.: US 10,247,721 B2
(45) Date of Patent: Apr. 2, 2019

(54) DIAGNOSTIC METHOD AND SYSTEM

(71) Applicant: Cytosystems Limited, Craibstone (GB)

(72) Inventors: David Galloway, Craibstone (GB); Daniel Mark Maynard, Huntingdon (GB)

(*) Notice: Subject to any disclaimer, the term of this patent is extended or adjusted under 35 U.S.C. 154(b) by 343 days.

(21) Appl. No.: 15/010,227

(22) Filed: Jan. 29, 2016

(65) Prior Publication Data

US 2016/0146782 A1    May 26, 2016

Related U.S. Application Data

(63) Continuation of application No. 14/370,447, filed as application No. PCT/GB2013/000003 on Jan. 4, 2013, now abandoned.

(30) Foreign Application Priority Data

Jan. 6, 2012   (GB) .................................. 1200178.0

(51) Int. Cl.
| | | |
|---|---|---|
| G01N 33/50 | (2006.01) | |
| G01N 33/68 | (2006.01) | |
| G02B 21/36 | (2006.01) | |
| G06K 9/00 | (2006.01) | |
| G02B 21/26 | (2006.01) | |
| G01N 21/25 | (2006.01) | |

(52) U.S. Cl.
CPC ..... *G01N 33/5005* (2013.01); *G01N 33/6875* (2013.01); *G02B 21/26* (2013.01); *G02B 21/361* (2013.01); *G02B 21/365* (2013.01); *G06K 9/00147* (2013.01); *G01N 21/251* (2013.01); *G01N 2800/7028* (2013.01)

(58) Field of Classification Search
CPC ........... G01N 33/5005; G01N 33/6875; G01N 21/251; G01N 2800/7028; G02B 21/361; G02B 21/26; G02B 21/365; G06K 9/00147

See application file for complete search history.

(56) References Cited

U.S. PATENT DOCUMENTS

| | | | |
|---|---|---|---|
| 5,134,662 A | | 7/1992 | Bacus et al. |
| 5,281,517 A | * | 1/1994 | Bacus ................ G01N 15/1468 356/39 |
| 6,656,683 B1 | | 12/2003 | Reuben et al. |
| 2002/0164063 A1 | | 11/2002 | Heckman |

(Continued)

OTHER PUBLICATIONS

Search Report dated Apr. 29, 2013, in corresponding International Application No. PCT/GB2013/000003.

(Continued)

*Primary Examiner* — Yon J Couso
(74) *Attorney, Agent, or Firm* — Gary Baker; Quine IP Law

(57) ABSTRACT

The present invention relates to a method of diagnosis which identifies one or more individual cells and comprises determining at least one of a cell dimension and a cell area, and determining at least one of dark/light cell contrast characteristics, cell area characteristics, cell color characteristics, cell roughness characteristics, distances between cell nuclei and cell convexity. A computer readable medium, a computer apparatus and a diagnostic system is also provided.

20 Claims, 2 Drawing Sheets

(56) References Cited

U.S. PATENT DOCUMENTS

| | | | |
|---|---|---|---|
| 2005/0260566 A1* | 11/2005 | Fischer | C07K 16/3069 435/5 |
| 2009/0214096 A1* | 8/2009 | Andrushkiw | G06T 7/0012 382/131 |
| 2009/0317836 A1* | 12/2009 | Kuhn | G01N 33/574 435/7.23 |
| 2011/0111435 A1* | 5/2011 | Dobson | G01N 33/566 435/7.23 |
| 2011/0188728 A1 | 8/2011 | Sammak et al. | |

OTHER PUBLICATIONS

Anonymous (2011) "Scorpion Vision Based Cancer Detection System Unveiled." Retrieved from the Internet: http://scorpionvision.co.uk/announcements/scorpion-vision-based-cancer-detection-system-unveiled; https://tordivelblog.com/2011/11/08/scorpion-vision-based-cancer-detection-system-unveiled.

Donnini, et al. (2011) "Pilot study using an automated digital counting microscope in urine cytology." 7th NCRI Cancer Conference, Nov. 6, 2011, BT Convention Centre, Liverpool, UK. Retrieved from the Internet: http://www.ncri.org.uk/ncriconference/2011abstracts/abstracts/LB7.html; http://conference.ncri.org.uk/abstracts/2011/abstracts/LB7.html.

Paul (2009) "Scorpion Vision for biomedical analyses." Scorpion Vision Web Shop Blog, Retrieved from the Internet: http://scorpionvision.wordpress.com/2009/04/24/scorpion-vision-for-biomedical-analyses/.

Donnini ,et. al. (2011) "Pilot study using an automated digital counting microscope in urine cytology." Poster presented at the 7th NC RIU Cancer Conference, Nov. 6-9, 2011, BT Convention Center, Liverpool, UK. Retrieved from the internet: http://scorpionvision.co.uk/newsletters/Cytology%20Pilot%20System.pdf.

* cited by examiner

DIAGNOSTIC METHOD AND SYSTEM

This application is a continuation of U.S. application Ser. No. 14/370,447 filed Jul. 2, 2014 which is a U.S. National Phase of PCT Patent Application No. PCT/GB2013/000003 filed Jan. 4, 2013 which claims priority to United Kingdom Patent Application No. GB 1200178.0 filed Jan. 6, 2012, the disclosures of which are incorporated herein by reference in their entirety for all purposes.

FIELD OF THE INVENTION

The present invention relates to diagnostic methods and systems and particularly to diagnostic methods and systems for analysing abnormal cells and more particularly to analysing abnormal cells for the diagnosis of cancers.

BACKGROUND OF THE INVENTION

The diagnostic method of taking cells from living organs, processing the cells using, for example, a colour dye, and then observing the cells under a microscope for abnormalities, has been used for many years. One such example is the "Pap" smear test, which is widely used to screen for cervical cancer in women.

This known diagnostic method is carried out by skilled operators. However, in being a human activity and due to the relatively large number of cells and cell characteristics which are required to be viewed, it is inevitable that there is a degree of subjectivity in determining abnormal cells. Furthermore, the requirement of a skilled operator means that it is a relatively expensive procedure and inhibits a wider application where there is a skills shortage.

Such diagnostic methods using routine cytology are carried out to investigate a variety of different conditions such as, for example, cervical cancer with the "Pap test", cancer of the oesophagus and diseases of the urinary tract.

Cancer of the bladder is currently the fourth most common cancer in men and the seventh most common cancer in women. The condition is currently investigated by cystoscopy to observe signs of malignancy. It is estimated that up to 3.6 million cystoscopies for TCC (Transitional Cell Carcinoma of the bladder) are carried out each year in Europe and the USA. However, cystoscopy is a relatively expensive procedure to administer and it is also an intrusive procedure and can be uncomfortable for the patient, who requires a local or general anaesthetic. Moreover, post-treatment bladder cancer patients often have to undergo a large number of surveillance cystoscopies for life.

The above-mentioned disadvantages are also relevant and equally applicable to other diagnostic methods and the diagnosis of other diseases, particularly other cancers.

It is an object of the present invention to at least substantially mitigate these disadvantages. It is also an object of the present invention to provide a cost effective and standardised method and system for analysing abnormal cells and more particularly to the analysis of abnormal cells for the diagnosis of cancers.

STATEMENTS OF INVENTION

According to a first aspect of the present invention there is provided a method of diagnosis comprising:
observing one or more cell samples; identifying one or more individual cells; determining one or more characteristics of the, or each, individual cell; comparing the, or each, determined characteristic with a respective determined or predetermined characteristic; and recording the correlation of the, or each, determined characteristic and the respective predetermined characteristic; wherein identifying the one or more individual cells comprises determining at least one of a cell dimension and a cell area, and wherein determining the one or more characteristics comprises determining at least one of the dark/light cell contrast characteristics, cell area characteristics, cell colour characteristics, cell roughness characteristics, distances between cell nuclei and cell convexity.

The method advantageously further comprises providing image processing means; receiving an image of the one or more cell samples; identifying one or more individual cells on the received image; determining one or more characteristics of the, or each, individual cell from the captured image;
comparing the, or each, determined characteristic with a respective determined or predetermined characteristic; and
recording the correlation of the, or each, determined characteristic and the respective predetermined characteristic; wherein identifying the one or more individual cells comprises the image processing means determining at least one of a cell dimension and a cell area, and wherein determining the one or more characteristics comprises the image processing means determining at least one of the dark/light cell contrast characteristics, cell area characteristics, cell colour characteristics, cell roughness characteristics, distances between cell nuclei and cell convexity.

The method preferably comprises the steps of:
(i) isolating cells from the sample to provide a cell sample;
(ii) contacting said cell sample with an antibody capable of binding a minichromosome maintenance (MCM) polypeptide(s); and
(iii) determining the binding of said antibody to the cell sample.

The MCM is selected from the group consisting of MCM 2, 3, 4, 5, 6 and 7. The MCM may be a combination of two or more different MCMs, for example, two different MCMs selected from the group consisting of MCM 2, 3, 4, 5, 6 and 7. For example the MCM may include MCM2 and one other MCM selected from MCM 3, 4, 5, 6 and 7. By way of further example the MCM may include MCMS and one other MCM selected from MCM 2, 3, 4, 6 and 7. In a preferred method of the invention, the MCM is selected from the group consisting of MCM 2, 3, 5 and 7. In a further preferred method of the invention, the MCM is selected from the group consisting of MCM 2, 5 and 7.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies (i.e. protein fragments). Antibodies may be polyclonal or monoclonal.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic.

Antibodies which are specific for a MCM may be obtained using techniques which are standard in the art. Methods of producing antibodies include immunising a mammal (e.g. mouse, rat, rabbit) with the protein or a fragment thereof or a cell or virus which expresses the protein or fragment.

"Specific" is generally used to refer to the situation in which one member of a specific binding pair will not show any significant binding to molecules other than its specific binding partner(s), e.g., has less than about 30%, preferably 20%, 10%, or 1% cross-reactivity with any other molecule.

The antibody may be a monoclonal antibody having an antigen binding domain specific for MCM. Monoclonal antibodies specific for MCM are known in the art, for example, anti-MCM2 antibody may be obtained from the Cancer Cell Unit, Hutchison/MRC Research Centre, Hills Road, Cambridge CB2 0XZ.

The specific antibody may be labelled with a detectable label, for example a radiolabel such as Iodine or 99Tc, which may be attached to the antibody using conventional chemistry known in the art of antibody imaging. Such labelling allows those cells that are bound to the antibody to be detected/visualised. Labels also include enzyme labels such as horseradish peroxidase or alkaline phosphatase. Labels further include chemical moieties such as biotin which may be detected via binding to a specific cognate detectable moiety, e.g. labelled avidin.

The reactivities of an antibody on normal and test samples may be determined by any appropriate means. Other labels include fluorochromes, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Alkaline phosphatase or horseradish peroxidase are generally employed.

The method advantageously further comprises summing the number of individual cells which have determined characteristics which correlate with the predetermined characteristics.

The method advantageously further comprises scanning a tissue or cytology sample to provide the image of the one or more cell samples.

The scanning preferably comprises raster scanning.

The method advantageously further comprises staining (i.e. dying) a said tissue or cytology sample prior to scanning.

The step of identifying the individual cells advantageously comprises identifying respective nuclei on the image.

The nuclei may be identified by determining dark areas of the image.

The method advantageously further comprises determining the intensity of the contrast of the dark/light image areas of the said cell.

The method advantageously further comprises searching for coloured regions of the cell on the image.

The step of determining the cell dimension advantageously comprises the image processing means determining one or more of the cell contour area, cell circularity, cell axis ratio, cell length and cell width.

According to a second aspect of the present invention, there is provided a computer readable medium carrying a computer program configured to carry out the method of the first aspect of the present invention.

According to a third aspect of the present invention, there is provided a computer apparatus comprising:
 a memory storing processor readable instructions; and
 a processor configured to read and execute instructions stored in said program memory;
 wherein said processor readable instructions comprise instructions controlling the processor to carry out the method according to the first aspect of the present invention.

According to a fourth aspect of the present invention there is provided a diagnostic system comprising:
 a sample slide mount for receiving a slide having cell samples disposed thereon;
 image capture means operable to capture an image of the cell samples; and
 a computer apparatus according to the third aspect of the present invention.

The image capture means preferably comprises magnifying means. The magnifying means is preferably a microscope.

The system may further comprise a motor operable to move the sample slide mount relative to the image capture means in a controlled manner. The motor preferably comprises a faster scanner to move the sample slide mount relative to the image capture means in a controlled manner.

Throughout the description and claims of this specification, the words "comprise" and "contain" and variations of the words, for example "comprising" and "comprises", means "including but not limited to", and is not intended to (and does not) exclude other additives, components, integers or steps.

Throughout the description and the claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The present invention will now be described by way of example only with reference to drawings, in which.

DETAILED DESCRIPTION OF THE INVENTION

I. Introduction

Figure 1:
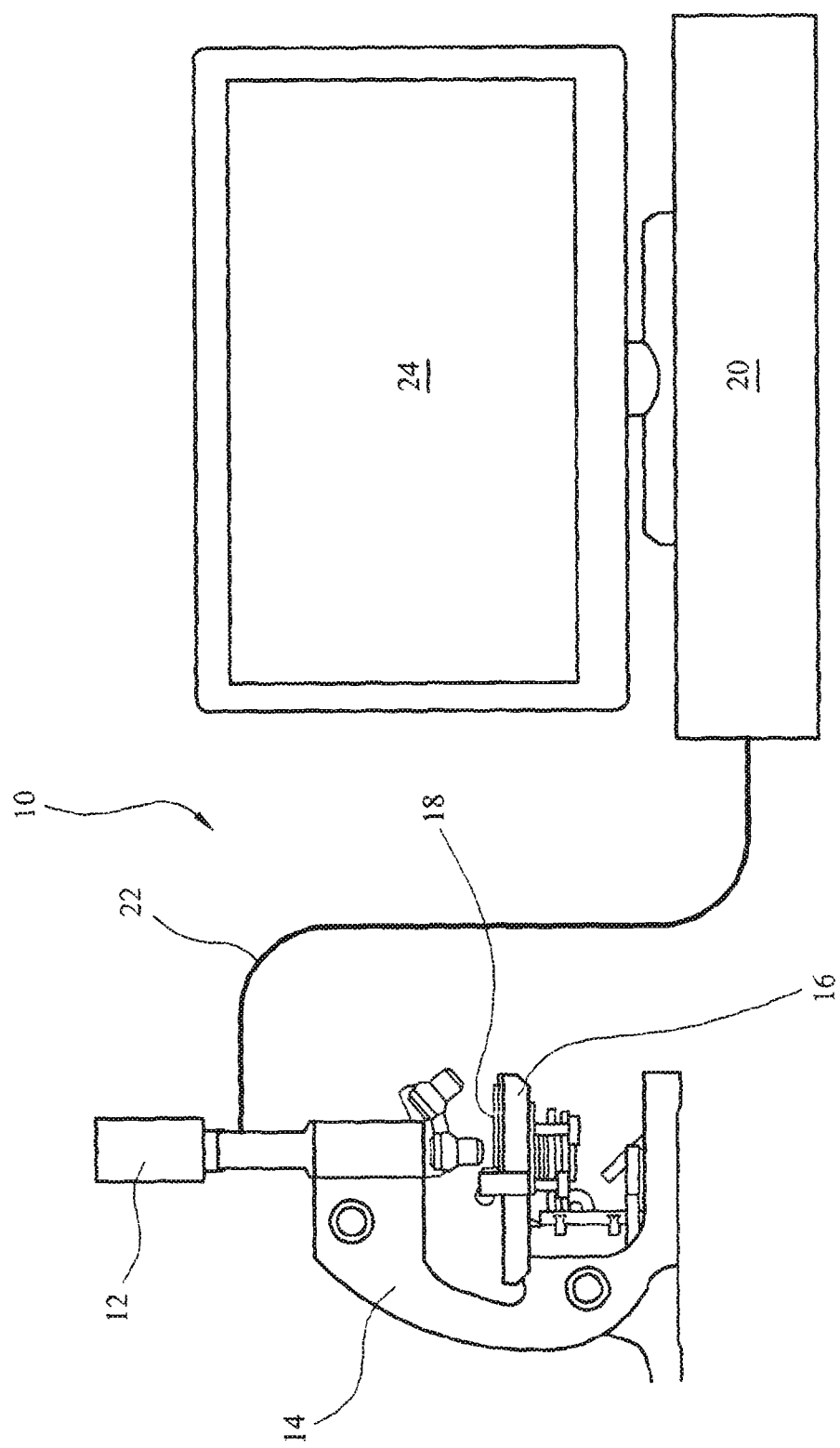
FIG. 1 is a schematic drawing showing a diagnostic system according to one aspect of the present invention.

Referring to FIG. 1, a diagnostic system 10, according to the present invention, comprises image capture means, such as a still or video camera 12. The camera 12 is mounted on magnifying means, such as a microscope 14. The microscope 14 has a sample slide mount 16, for receiving a slide (e.g. a cytology slide) 18 having sample cells disposed thereon. The slide mount 16 is moveable relative to the camera 12 in a controlled manner in order to provide a raster scanning function.

The diagnostic system 10 further comprises a computer processor 20, which is electrically connected to the camera 12 and microscope 14 by a communication link 22, such that the images captured by the camera are transmittable to the processor 20 and the computer processor can control focusing of the camera and scanning movements of the slide mount.

The system further comprises a computer VDU 24, for displaying images and data.

Prior to undertaking an analysis, using the diagnostic method of the present invention, the cell samples are advantageously processed. For example, human bladder cells are processed with minichromosome maintenance proteins (MCM). Processing bladder cells with MCM provides a colour change in the nuclei of the cells which is indicative of cell turnover rate which may be an indication for cancer. It will be appreciated that other stains (i.e. dyes) and processes may be used in relation to other types of cells and diagnostic methods within the working of the present invention.

Although, the diagnostic method of the present invention will be described herein with reference to the diagnosis of bladder cancer, it will be appreciated that the method is equally applicable to the analysis of other cells, such as, for example, prostrate, lung, cervical and colo-rectal cells and, moreover, that the method is equally applicable to automated slide (e.g. cytology slide or histology slide) analysis in other areas of diagnosis or monitoring.

Figure 2:
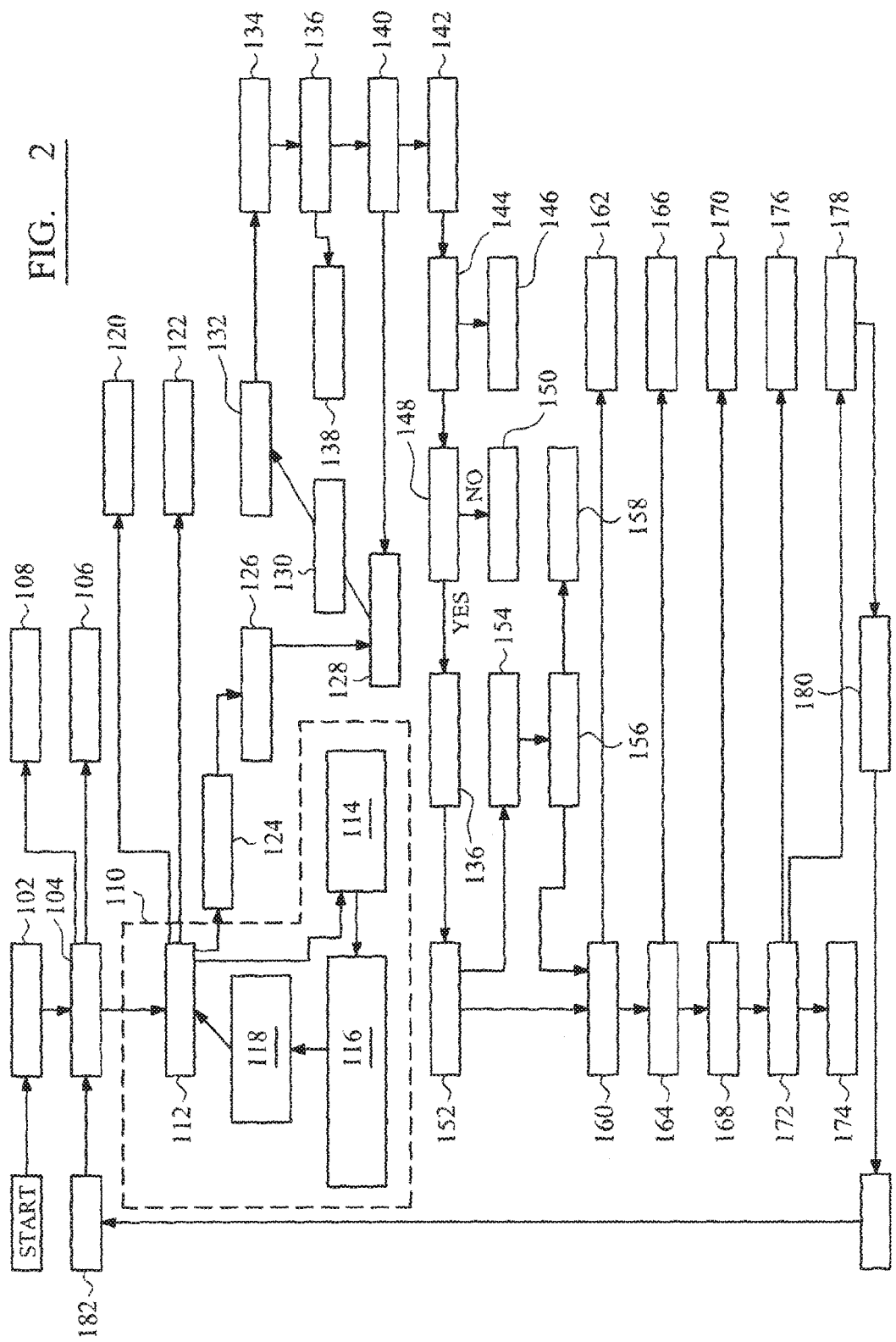
FIG. 2 is a flow diagram showing a diagnostic method according to another aspect of the present invention.

Referring also to FIG. 2, the diagnostic method is undertaken through a computer program stored in computer processor 20.

The diagnostic method is started by carrying out a slide positioning step 102, in which a slide 18, on which cell samples are disposed, is positioned on the slide mount 16 in a first field location. Typically, the cell samples cover a sample area of approximately 10 mm to approximately 20 mm in diameter on the slide (e.g. 13 mm to 20 mm) and a field is a portion of the sample area. There is therefore a plurality of fields within each sample area.

A scanning step 104 is then undertaken in which the positioned first field is focused 106 through the lenses of the microscope 14. Mechanical focusing of the first field through the microscope is achieved using an edge-based algorithm. If sample cells are not detected, within the first field, focusing is not carried out and the slide is indexed to the next positioned field 108. The scanning step 104 is then repeated for the next positioned field. However, if sample cells are detected, the focused first field is scanned and the image is recorded using the camera 12 and stored in memory within the computer processor. The scanning step 104 involves faster scanning the sample cells.

The method then comprises a cell identification step 110 in which the individual sample cells are identified on the slide 18. This is carried out using image processing to locate areas of the image which match specific predetermined characteristics indicative of the presence of a cell of interest, such as, for example, for bladder cells the predetermined characteristics may be: initial location and dimensions of cytoplasm outline 112 which correlate with predetermined criteria; location and dimensions of dark areas (e.g. brown) 118 which correlate with predetermined criteria to indicate the presence of a nucleus; location and dimensions of cytoplasm using light/dark contrast analysis 120, which correlate with predetermined criteria; and analysis of colour matching 122 to correlate with predetermined criteria.

For bladder cells the criteria for the location and dimensions of the cytoplasm outline 112 are a length greater than a length in the range of approximately 5 to 15 μm (preferably 9 μm), a width greater than a width in the range of approximately 5 to 15 μm (preferably 8 μm) and an area greater than an area in the range of approximately 5-250 μm (preferably 5 μm2). The criteria for the location and dimensions of dark areas (e.g. brown) 118 includes a contour area of greater than an area in the range of approximately 5-250 μm2 (preferably 25 μm2) and less than an area in the range of approximately 1000 μm2 to 5000 μm2 (preferably 2500 μm2) and a minimum circularity in the range of approximately 0.01 to 0.1 (preferably 0.05). The cells are checked 120 and are deemed to be acceptable if the cell area is greater than an area in the range of approximately 100 to 1000 μm2 (preferably 500 μm2) and has a dark cytoplasm area greater than 5 μm2 (preferably 40 μm2) and less than 500 μm2 (preferably 250 μm2) and a cell contrast greater than a specific value in the range of 10 to 60 (preferably 35□. The colour matching analysis 122 requires a search for dark areas and determining whether the colour of the dark area falls within the range of the values of hue, saturation and intensity of a predetermined area. Thus, the threshold may be 0-120 and the predetermined area may be an area greater then an area in the range of 5-250 μm2 (e.g. 25 μm2). For the avoidance of doubt, where ranges are provided, the criteria may be set at any value within that range. Clearly, the value used will be consistent throughout the process.

When analysing bladder cells during the initial step of determining the location and dimensions of cytoplasm outlines 112, if anything is detected which has a cell length of less than the defined criteria for cell length (e.g. less than a length in the range of approximately 5 to 15 μm, preferably 9 μm) and a cell width of less than the defined criteria for cell width (e.g. less than a width in the range of approximately 5 to 15 μm, preferably 8 μm) it is not considered relevant and instead considered to be debris and not counted 114. Similarly, if anything is detected which has a cell area less than the predetermined value (e.g. less than an area in the range of 5-250 μm2, e.g. 5 μm2) it is not considered relevant and instead considered to be debris and not counted 116.

The individual analysis starts with an analysis of the nucleus.

The analysis of the nucleus begins with a check for a distinct nucleus whereby the image of the selected cell is analysed to determine the nucleus. This initially involves testing the dark areas for a fit into a defined area (bounding box) 124. If the length of the cell nucleus bounding box is greater than a length in the range of 5 to 15 μm (preferably 12 μm) then it is determined that there is a cluster of nuclei and the cluster is split into individual centres 126 prior to looping through identifiable dark areas 128, whereas if the cell nucleus bounding box 124 is lower than the defined value, no splitting step 126 is necessary prior to lopping through dark areas 128. Looping though dark areas may be indicative of the location of a nucleus within the cytoplasm of the selected cell image. Then the area inside the dark area contour is divided by the area of the smallest rectangle that can be fit around the same contour 130 to provide a ratio. Suitably, the minimum ratio is a ratio in the range of 0.2 to 0.6 (preferably 0.4). The degree of dark/light contrast of the dark area relative to the cytoplasm is then determined 132 whereby a minimum level of contrast is required to ascertain a distinct nucleus. The minimal level of contrast may be set at a value in the range of 10 to 60 (preferably 35).

If the criterion of the steps 124 to 132 is within the relevant thresholds then the nucleus is considered to be distinct which is indicative of the presence of the cell [any type of cell] and the cell is added to a Field Total Cell Count (FTCC) 134 which is recorded in memory 136.

For each distinct nucleus, the method further comprises a step of determining the nucleus intensity 138. If the intensity is less than a defined intensity in the range of 60 to 150 (preferably 120), the method further comprises a colour matching step 142. If the intensity is greater than the defined intensity, the cell is considered not to be relevant for the cell count which is recorded accordingly 140.

The colour matching step 142 comprises the signal processing determining the colours of the nucleus of cells which match a predetermined range of colour indicative of the presence of disease.

If the colour matching step 142 does not result in the detection of any distinct colours or if distinct colours are detected but the detected colours do not match the predetermined colour (i.e. no match) then the cell is considered not to be relevant for the cell count which is recorded accordingly 144.

If the colour matching step 142 results in a positive outcome (i.e., colour match detected—for example, for bladder cells processed with MCM a dark coloured stain (e.g., brown coloured) in the nucleus is indicative of cell turnover rate which may be indicative of the presence of cancer) then it is added to a Field Colour Match Total (FCMT) count 146. The FCMT count 146 is the sum of the FICC counts 136 minus the number of high nucleus intensity cells 140 and minus the number of no colour match cells 144.

The number of cells having particular stain characteristics can be significant for diagnoses. Therefore, checking so-called "raspberry clumps", where a number of cells are in contact with each other, is important as one or more cells within a clump may be significant for a diagnosis and others may not.

In order to take this into account, the method further comprises the step of determining whether there are more than a set number of nuclei present 148, wherein the set number is in the range of 4 to 8 (preferably 4) and, if so, calculates: the distance between nuclei using mean and standard deviation to nearest neighbour, overall area and axis ratio of cytoplasm 150 to ascertain whether or not it is indicative of a "raspberry clump".

Nuclei touching each other can be difficult to define. However, this has been achieved whereby the image processing identifies the darker centre of each nucleus in the clump. Additionally, or alternatively, the image processing defines the shape of the outline contour of the each nucleus.

If it is determined that there is a "raspberry clump" it is considered a field positive cell and recorded accordingly 172.

If it is determined that the there are not more than four nuclei present (under step 148) or that there are more than four nuclei present (under step 148) and a "raspberry clump" is also determined not to be present (under step 150), the method proceeds to cell exclusion steps 152 and 156 which determines non-viable cells and macrophage cells. The cell exclusion step involves the image processing determining the roughness of the cell by analysing the intensity in the gradient of the image of the cell. The analysis may be undertaken on the cytoplasm and/or the nucleus of the cell.

If the roughness of the cytoplasm is determined to be greater than a set value in the range of 5 to 25, preferably 15 (under step 152), the cell is considered not to be relevant for the cell count which is recorded accordingly 154.

If the roughness of the nucleus is determined to be greater than a set value in the range of 5 to 25, preferably 12 (under step 156), the cell is considered not to be relevant for the cell count which is recorded accordingly 158.

The method further comprises a nucleus contour analysis step 160 which determines the roughness of the contour edge of the nucleus. This step involves the image processing determining the roughness of the nucleus contour edge by analysing the intensity in the gradient of the image of the nucleus. If the contour roughness is determined to be too rough the nucleus is likely to be degenerative.

If the intensity in the gradient is determined to be less than a set value in the range of 20 to 40 (preferably 30) then the cell is considered not to be relevant for the cell count which is recorded accordingly 162.

If the intensity in the gradient is determined to be greater than the set value in the range of 20 to 40 (preferably 30) then the cell is checked for coloured stain in the cytoplasm 164.

If stain is detected in the cytoplasm of the cell in step 164 then the cell is considered not to be relevant for the cell count which is recorded accordingly 166.

If a stain is not detected in the cytoplasm of the cell in step 164 then it proceeds to the small nuclei exclusion step 168.

The presence of large nuclei is considered to be more indicative of disease and therefore step 168 eliminates nuclei which are relatively small in size from the cell count. The image processing undertakes step 168 by determining a ratio of the size of the nucleus of the cell relative to the cytoplasm and comparing the ratio to a predetermined ratio. Any nuclei which are determined to be relatively small based on the predetermined ratio (i.e. less than a set value in the range of 0.2 to 0.4, preferably 0.32) are considered not to be relevant for the cell count which is recorded accordingly 170. Any nuclei which are determined to be greater than the predetermined ratio are considered to be field +ve cells and are recorded accordingly 172.

Another optional step which may be undertaken prior to record of the nuclei as field +ve is whereby the image processing measures the nucleus convexity (not shown). A positive, viable nucleus is considered to have a definite edge and be mostly convex. Therefore, a cell not having such a nucleus would be excluded from the cell count.

The Field +ve cells which are relevant for the diagnosis are then summed and recorded for the current field of interest 172, whereby the relevant cell count for the field is FMCM=FCMT(step 146)−C1(step 154)−C2(step 158)−C3 (step 162)−C4(step 166)−C5(step 170).

A Slide Total Cell Count (STCC) 174 is also summed as the analysis of each field of the sample cells disposed on the slide is completed.

A Slide Colour Match Total (SCMT) 176 is also summed whereby SCMT=SCMT (for each analysed field)+FCMT (step 146).

A Slide +ve Total Cell Count (SMCM) 178 is also summed whereby SMCM=SMCM (for each analysed field)+FMCM (Step 172).

After completion of the image processing analysis of the first field, the field location is incremented 108 to the second field area of the sample cells, the second field is scanned and the method continues therefrom as described above with reference to the image processing analysis of the first field.

In an exemplary embodiment, the invention provides a method as substantially described herein with reference to the accompanying drawings. In one embodiment, the invention provides a computer readable medium and a computer apparatus as substantially described herein with reference to the accompanying drawings. In an exemplary embodiment, the invention provides a system as substantially described herein with reference to the accompanying drawings.

In an exemplary embodiment, the invention provides a method as substantially described herein with reference to the accompanying drawings. In one embodiment, the invention provides a computer readable medium and a computer apparatus as substantially described herein with reference to the accompanying drawings. In an exemplary embodiment, the invention provides a system as substantially described herein with reference to the accompany drawings.

What is claimed is:

1. A method of diagnosis comprising:
   providing a sample comprising one or more cells;
   contacting said sample with an antibody adapted to bind a minichromosome maintenance (MCM) polypeptide;
   observing one or more cells in the sample;
   identifying one or more individual observed cells;
   determining one or more characteristics of the one or more individual cells;
   comparing the one or more determined characteristics with a respective determined or predetermined characteristic; and
   recording a correlation of the one or more determined characteristics and the respective predetermined characteristic;
   wherein identifying the one or more individual cells comprises determining at least a cell dimension or a cell area, and
   wherein determining the one or more characteristics comprises determining at least two of: the dark/light cell contrast characteristics, cell area characteristics, cell colour characteristics, cell roughness characteristics, distances between cell nuclei and cell convexity.

2. The method of diagnosis as claimed in claim 1, further comprising:
   providing image processing means;
   receiving an image of the one or more cell samples;
   identifying said one or more individual cells on the received image;
   determining the one or more characteristics of the one or more individual cells from the captured image;
   comparing the one or more determined characteristics with a respective determined or predetermined characteristic; and
   recording the correlation of the one or more determined characteristics and the respective predetermined characteristic;
   wherein identifying the one or more individual cells comprises the image processing means determining at least one of a cell dimension and a cell area, and
   wherein determining the two or more characteristics comprises the image processing means determining at least one of: the dark/light cell contrast characteristics, cell area characteristics, cell colour characteristics, cell roughness characteristics, distances between cell nuclei and cell convexity.

3. The method as claimed in claim 1, further comprising summing the number of individual cells which have determined characteristics which correlate with the predetermined characteristics.

4. The method as claimed in claim 2, further comprising scanning a tissue sample to provide the image of the one or more cell samples.

5. The method as claimed in claim 1, wherein identifying the individual cells comprises identifying respective nuclei on the image.

6. The method as claimed in claim 5, wherein the nuclei are identified by determining dark areas of the image relative to the cytoplasm.

7. The method as claimed in claim 1, further comprising determining the intensity of the contrast of the dark/light image areas of the said cell.

8. The method as claimed in claim 1, further comprising searching for regions of predetermined colour of the cell on the image.

9. The method as claimed in claim 1, wherein determining the cell dimension comprises determining one or more of: a cell contour area, cell circularity, cell axis ratio, cell convexity, cell length and cell width.

10. A non-transitory computer readable medium carrying a computer program configured to carry out the method of claim 1.

11. A computer apparatus comprising:
    a non-transitory memory storing processor readable instructions; and
    a processor configured to read and execute instructions stored in said non-transitory memory;
    wherein said processor readable instructions comprise instructions controlling the processor to carry out the method of claim 1.

12. A diagnostic system comprising:
    a sample slide mount for receiving a slide having cell samples disposed thereon;
    image capture means operable to capture an image of the cell samples; and
    a computer apparatus as claimed in claim 11.

13. The diagnostic system as claimed in claim 12 wherein the image capture means comprises magnifying means.

14. The system as claimed in claim 13, wherein the magnifying means is a microscope.

15. The system as claimed in claim 12 further comprising a motor operable to move the sample slide mount relative to the image capture means in a controlled manner.

16. A system as claimed in claim 15, wherein the motor comprises a raster scanner.

17. The method of claim 1, wherein the determined characteristics of the identified cells are selected from the group consisting of: a ratio of a nuclear stained dark area over an area of the smallest rectangle to fit around the dark area, cell length to width cell axis ratio, nuclear membrane roughness, and cell membrane roughness.

18. The method of claim 17, wherein cells are bladder cells, and the antibody is against MCM2.

19. The method of claim 1, further comprising diagnosing a disease state based on the determined characteristics of the sample cells.

20. The method of claim 1, wherein said determining characteristics further comprises detecting the antibody in the cell nucleus, which antibody comprises a detectable label.

* * * * *